(12) United States Patent
Simms et al.

(10) Patent No.: US 11,684,363 B2
(45) Date of Patent: Jun. 27, 2023

(54) INTEGRATED TISSUE POSITIONING AND JAW ALIGNMENT FEATURES FOR SURGICAL STAPLER

(71) Applicant: Cilag GmbH International, Zug (CH)

(72) Inventors: Robert J. Simms, Liberty Township, OH (US); Douglas B. Hoffman, Harrison, OH (US); Jason E. Zerkle, Blanchester, OH (US); Charles J. Scheib, Loveland, OH (US); Janna B. Volz, Fort Thomas, KY (US)

(73) Assignee: Cilag GmbH International, Zug (CH)

( * ) Notice: Subject to any disclaimer, the term of this patent is extended or adjusted under 35 U.S.C. 154(b) by 469 days.

(21) Appl. No.: 16/843,953

(22) Filed: Apr. 9, 2020

(65) Prior Publication Data

US 2020/0297342 A1    Sep. 24, 2020

Related U.S. Application Data

(63) Continuation of application No. 15/335,785, filed on Oct. 27, 2016, now Pat. No. 10,687,807, which is a
(Continued)

(51) Int. Cl.
*A61B 17/08* (2006.01)
*A61B 17/072* (2006.01)
(Continued)

(52) U.S. Cl.
CPC .......... *A61B 17/072* (2013.01); *A61B 17/068* (2013.01); *A61B 17/0682* (2013.01);
(Continued)

(58) Field of Classification Search
CPC ........................ A61B 17/072; A61B 17/068
See application file for complete search history.

(56) References Cited

U.S. PATENT DOCUMENTS

| 3,252,643 A | * | 5/1966 | Alexcevich | .......... | A61B 17/072 |
|---|---|---|---|---|---|
| | | | | | 227/19 |
| 4,216,891 A | | 8/1980 | Behlke | | |

(Continued)

FOREIGN PATENT DOCUMENTS

| CN | 202568354 U | 12/2012 |
|---|---|---|
| EP | 0 40552 A2 | 5/1985 |

(Continued)

OTHER PUBLICATIONS

Canadian Office Action dated Sep. 8, 2020 for Application No. 2,903,118, 5 pages.

(Continued)

*Primary Examiner* — Praachi M Pathak
(74) *Attorney, Agent, or Firm* — Frost Brown Todd LLP

(57) ABSTRACT

An apparatus includes a body, a shaft in communication with the body, and an end effector in communication with the shaft. The end effector is operable to drive staples through tissue. The end effector comprises an anvil and a cartridge. The anvil is operable to move pivotally relative to the cartridge. The cartridge is positioned to drive staples upwardly toward the anvil. The cartridge comprises a plurality of protrusions operable to prevent lateral rocking of the anvil. The plurality of protrusions is pointed toward the anvil. In some versions, an alignment member and/or a lateral stabilization member may be used between the anvil and the cartridge.

20 Claims, 21 Drawing Sheets

Related U.S. Application Data continuation of application No. 13/780,106, filed on Feb. 28, 2013, now Pat. No. 9,517,065.

(51) Int. Cl.
  *A61B 17/068* (2006.01)
  *A61B 17/00* (2006.01)
  *A61B 90/00* (2016.01)

(52) U.S. Cl.
  CPC .......... *A61B 17/07207* (2013.01); *A61B 2017/00115* (2013.01); *A61B 2017/00398* (2013.01); *A61B 2017/07257* (2013.01); *A61B 2017/07271* (2013.01); *A61B 2017/07278* (2013.01); *A61B 2090/0807* (2016.02)

(56) References Cited

U.S. PATENT DOCUMENTS

| | | | |
|---|---|---|---|
| 4,383,634 A * | 5/1983 | Green | A61B 17/072 227/135 |
| 4,610,383 A * | 9/1986 | Rothfuss | A61B 17/07207 227/176.1 |
| 4,805,823 A | 2/1989 | Rothfuss | |
| 5,014,899 A * | 5/1991 | Presty | A61B 17/07207 227/19 |
| 5,217,460 A * | 6/1993 | Knoepfler | A61B 18/24 606/1 |
| 5,318,221 A | 6/1994 | Green et al. | |
| 5,415,334 A | 5/1995 | Williamson, IV et al. | |
| 5,433,721 A * | 7/1995 | Hooven | A61B 17/068 606/139 |
| 5,452,837 A * | 9/1995 | Williamson, IV | A61B 17/07207 227/176.1 |
| 5,465,894 A * | 11/1995 | Clark | A61B 17/072 227/19 |
| 5,465,895 A | 11/1995 | Knodel et al. | |
| 5,529,235 A * | 6/1996 | Boiarski | A61B 90/98 600/101 |
| 5,597,107 A | 1/1997 | Knodel et al. | |
| 5,632,432 A | 5/1997 | Schulze et al. | |
| 5,662,258 A | 9/1997 | Knodel et al. | |
| 5,662,667 A | 9/1997 | Knodel | |
| 5,673,840 A | 10/1997 | Schulze et al. | |
| 5,704,534 A | 1/1998 | Huitema et al. | |
| 5,709,334 A | 1/1998 | Sorrentino et al. | |
| 5,772,099 A * | 6/1998 | Gravener | A61B 17/07207 227/176.1 |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,905,057 B2 | 6/2005 | Swayze et al. | |
| 6,959,852 B2 | 11/2005 | Shelton, IV et al. | |
| 6,978,921 B2 | 12/2005 | Shelton, IV et al. | |
| 7,000,818 B2 | 2/2006 | Shelton, IV et al. | |
| 7,044,352 B2 | 5/2006 | Shelton, IV et al. | |
| 7,083,075 B2 | 8/2006 | Swayze et al. | |
| 7,143,923 B2 | 12/2006 | Shelton, IV et al. | |
| 7,143,926 B2 | 12/2006 | Shelton, IV et al. | |
| 7,303,108 B2 | 12/2007 | Shelton, IV et al. | |
| 7,364,061 B2 | 4/2008 | Swayze et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,524,320 B2 | 4/2009 | Tierney et al. | |
| 7,644,848 B2 | 1/2010 | Swayze et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,066,166 B2 * | 11/2011 | Demmy | A61B 17/105 227/175.1 |
| 8,210,411 B2 | 7/2012 | Yates et al. | |
| 8,328,061 B2 | 12/2012 | Kasvikis | |
| 8,397,972 B2 * | 3/2013 | Kostrzewski | A61B 17/07207 227/176.1 |
| 8,408,439 B2 | 4/2013 | Huang et al. | |
| 8,424,738 B2 * | 4/2013 | Kasvikis | A61B 17/068 227/176.1 |
| 8,453,914 B2 | 6/2013 | Laurent et al. | |
| 8,479,969 B2 | 7/2013 | Shelton, IV et al. | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV et al. | |
| 8,820,605 B2 | 9/2014 | Shelton, IV et al. | |
| 8,844,789 B2 | 9/2014 | Shelton, IV et al. | |
| 8,893,946 B2 * | 11/2014 | Boudreaux | A61B 17/29 606/205 |
| 8,899,461 B2 * | 12/2014 | Farascioni | A61B 17/07207 227/176.1 |
| 9,016,539 B2 * | 4/2015 | Kostrzewski | A61B 17/072 227/176.1 |
| 9,107,662 B2 * | 8/2015 | Kostrzewski | A61B 17/068 |
| 9,186,142 B2 | 11/2015 | Fanelli et al. | |
| 9,301,759 B2 | 4/2016 | Spivey et al. | |
| 9,386,988 B2 | 7/2016 | Baxter, III et al. | |
| 9,517,065 B2 | 12/2016 | Simms et al. | |
| 10,111,660 B2 * | 10/2018 | Hemmann | A61J 1/00 |
| 10,687,807 B2 | 6/2020 | Simms et al. | |
| 2006/0180634 A1 | 8/2006 | Shelton, IV et al. | |
| 2007/0010838 A1 | 1/2007 | Shelton, IV et al. | |
| 2007/0084897 A1 | 4/2007 | Shelton, IV et al. | |
| 2007/0175955 A1 | 8/2007 | Shelton, IV et al. | |
| 2009/0012556 A1 * | 1/2009 | Boudreaux | A61B 90/06 600/587 |
| 2011/0186614 A1 * | 8/2011 | Kasvikis | A61B 17/068 227/176.1 |
| 2012/0074198 A1 | 3/2012 | Huitema et al. | |
| 2012/0248169 A1 | 10/2012 | Widenhouse et al. | |
| 2014/0224686 A1 * | 8/2014 | Aronhalt | A61B 17/068 206/339 |
| 2014/0239036 A1 * | 8/2014 | Zerkle | A61B 17/068 227/175.1 |
| 2014/0239037 A1 | 8/2014 | Boudreaux et al. | |
| 2014/0239038 A1 | 8/2014 | Leimbach et al. | |
| 2014/0239041 A1 | 8/2014 | Zerkle et al. | |
| 2014/0239044 A1 | 8/2014 | Hoffman | |

FOREIGN PATENT DOCUMENTS

| | | |
|---|---|---|
| EP | 1254636 A2 | 11/2002 |
| EP | 1690502 A1 | 8/2006 |
| EP | 1767157 A1 | 3/2007 |
| EP | 2248473 A2 | 11/2010 |
| JP | 2006-525090 A | 11/2006 |
| JP | 2007-090070 A | 4/2007 |
| JP | 2009-018163 A | 1/2009 |
| RU | 2161450 C1 | 1/2001 |
| WO | WO 2003/094746 A1 | 11/2003 |

OTHER PUBLICATIONS

European Communication dated Jun. 30, 2020 for Application No. 14157371.7, 8 pages.
Canadian Office Action dated Feb. 7, 2020 for Application No. 2,903,118, 4 pages.
Chinese Office Action, The Second Office Action, dated Sep. 27, 2017 for Application No. 201480010840.4, 5 pages.
Partial European Search Report dated Jun. 4, 2014 for Application No. 14157371.7, 8 pages.
Extended European Search Report dated Oct. 22, 2014 for Application No. 14157371.7, 12 pages.

(56) References Cited

OTHER PUBLICATIONS

European Exam Report dated Apr. 11, 2017 for Application No. 14157371.7, 6 pages.
International Search Report and Written Opinion dated Nov. 12, 2014 for International Application No. PCT/US2014/016203, 20 pages.
International Preliminary Report on Patentability dated Sep. 1, 2015 for International Application No. PCT/US2014/016203, 13 pages.
Japanese Office Action, Notification of Reasons for Refusal, and Search Report by Registered Searching Organization, dated Nov. 14, 2017 for Application No. 2015-560200, 14 pages.
Japanese Office Action, Notification of Reasons for Refusal, dated Jul. 3, 2018 for Application No. 2015-560200, 4 pages.
Japanese Office Action, Decision of Refusal, dated Mar. 5, 2019, for Application No. 2015-560200, 4 pages.
Japanese Office Action, Decision to Grant, dated Jul. 9, 2019 for Application No. 2015-560200, 2 pages.
Russian Search Report dated May 4, 2018 for Application No. 2015140759/14, 2 pages.

\* cited by examiner

INTEGRATED TISSUE POSITIONING AND JAW ALIGNMENT FEATURES FOR SURGICAL STAPLER

This application is a continuation of U.S. patent application Ser. No. 15/335,785, entitled "Integrated Tissue Positioning and Jaw Alignment Features for Surgical Stapler," filed Oct. 27, 2016, published as U.S. Pub. No. 2017/0042537 on Feb. 16, 2017, issued as U.S. Pat. No. 10,687,807 on Jun. 23, 2020, which is a continuation of U.S. patent application Ser. No. 13/780,106, entitled "Integrated Tissue Positioning and Jaw Alignment Features for Surgical Stapler," filed Feb. 28, 2013, issued as U.S. Pat. No. 9,517,065 on Dec. 13, 2016.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed ends of the tissue layers together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, now U.S. Pat. No. 8,408,439, issued Apr. 2, 2013; and U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued Jun. 4, 2013. The disclosure of each of the above-cited U.S. Patents and U.S. Patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain, the principles of the present invention.

Figure 1:
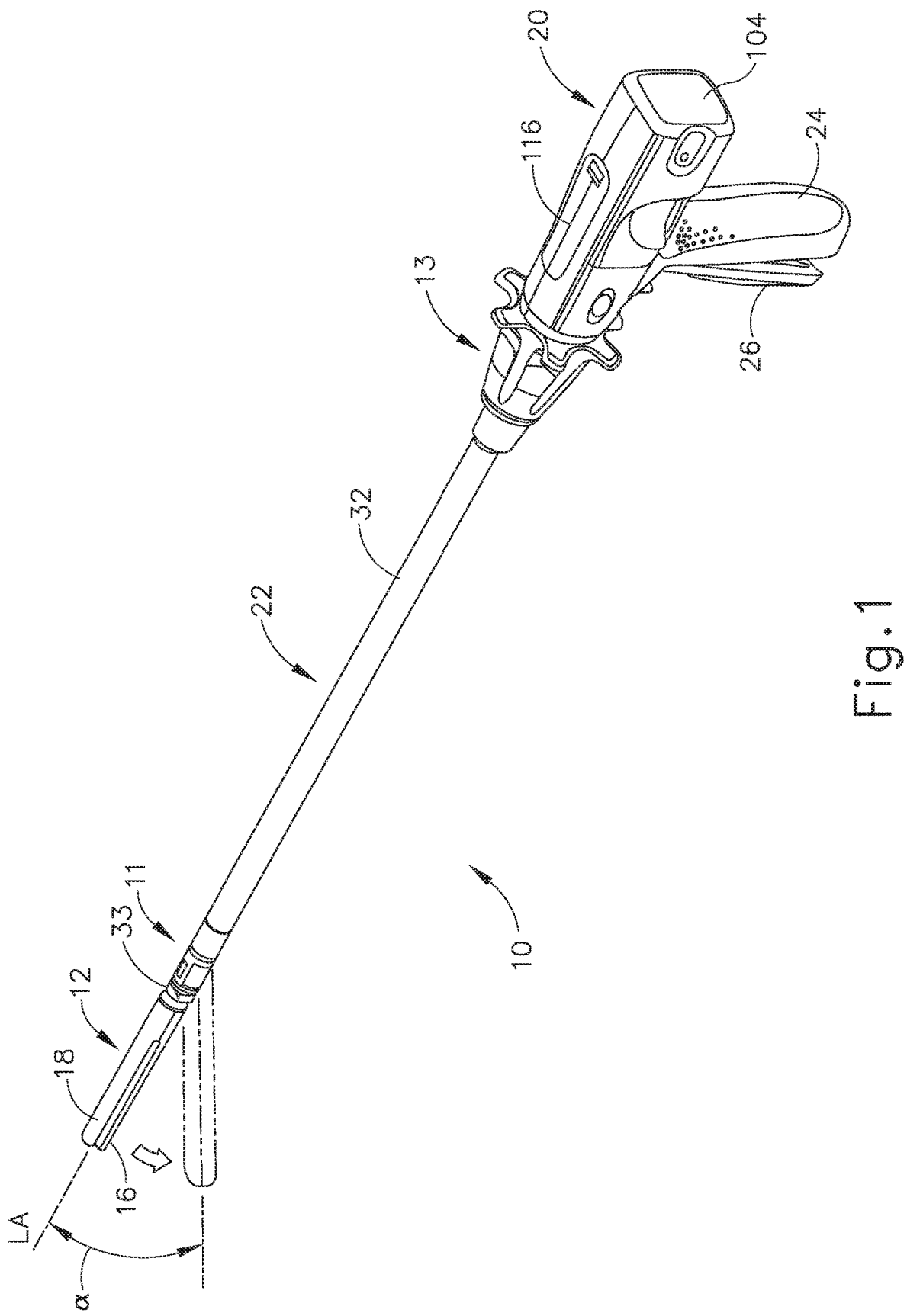
FIG. 1 depicts a perspective view of an exemplary articulating surgical stapling instrument.
Figure 2:
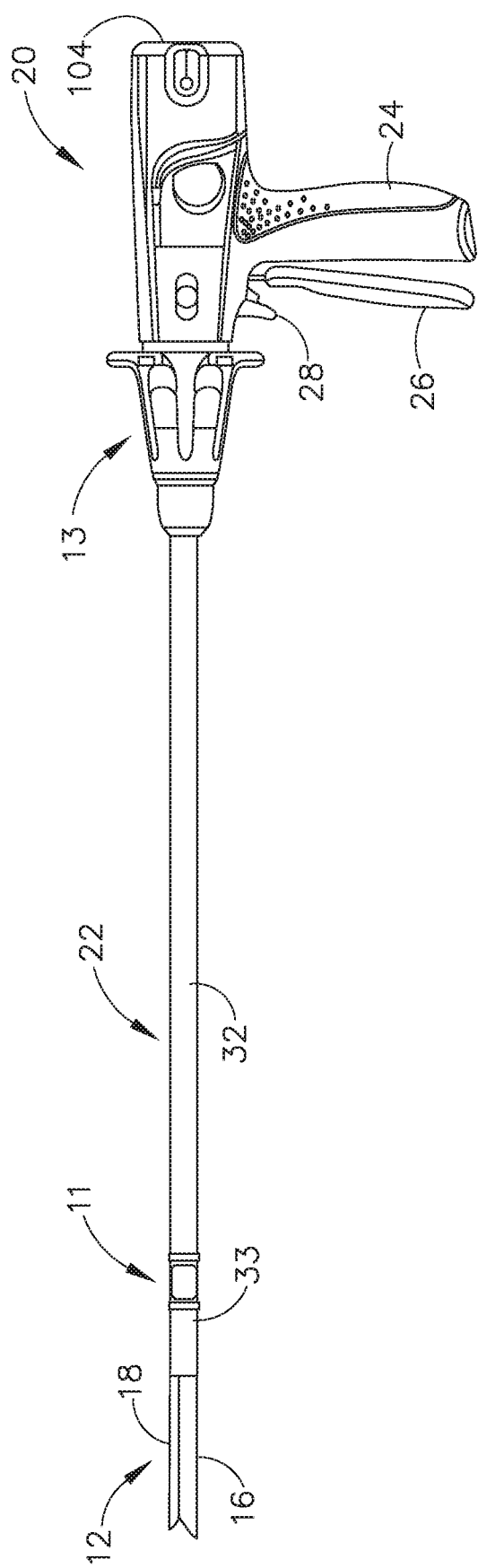
FIG. 2 depicts a side elevational view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

In some versions, shaft (22) is constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle ($\alpha$). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein. Articulation joint (11) may also be constructed and operable in accordance with at least some of the teachings of U.S. Pat. No. 9,795,379, issued Oct. 24, 2017, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In some versions, lower jaw (16) is constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Various exemplary alternative features, configurations, and operabilities that may be incorporated into anvil (18) will be described in greater detail below. In addition, anvil (18) may be constructed in accordance with at least some of the teachings of U.S. Pat.

No. 10,092,292, entitled "Staple Forming Features for Surgical Stapling Instrument," issued Oct. 9, 2018, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate: member (136) (shown in FIG. 11) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein. Other suitable forms that firing beam (14) may take will be apparent to those of ordinary skill in the art in view of the teachings herein.

Figure 3:
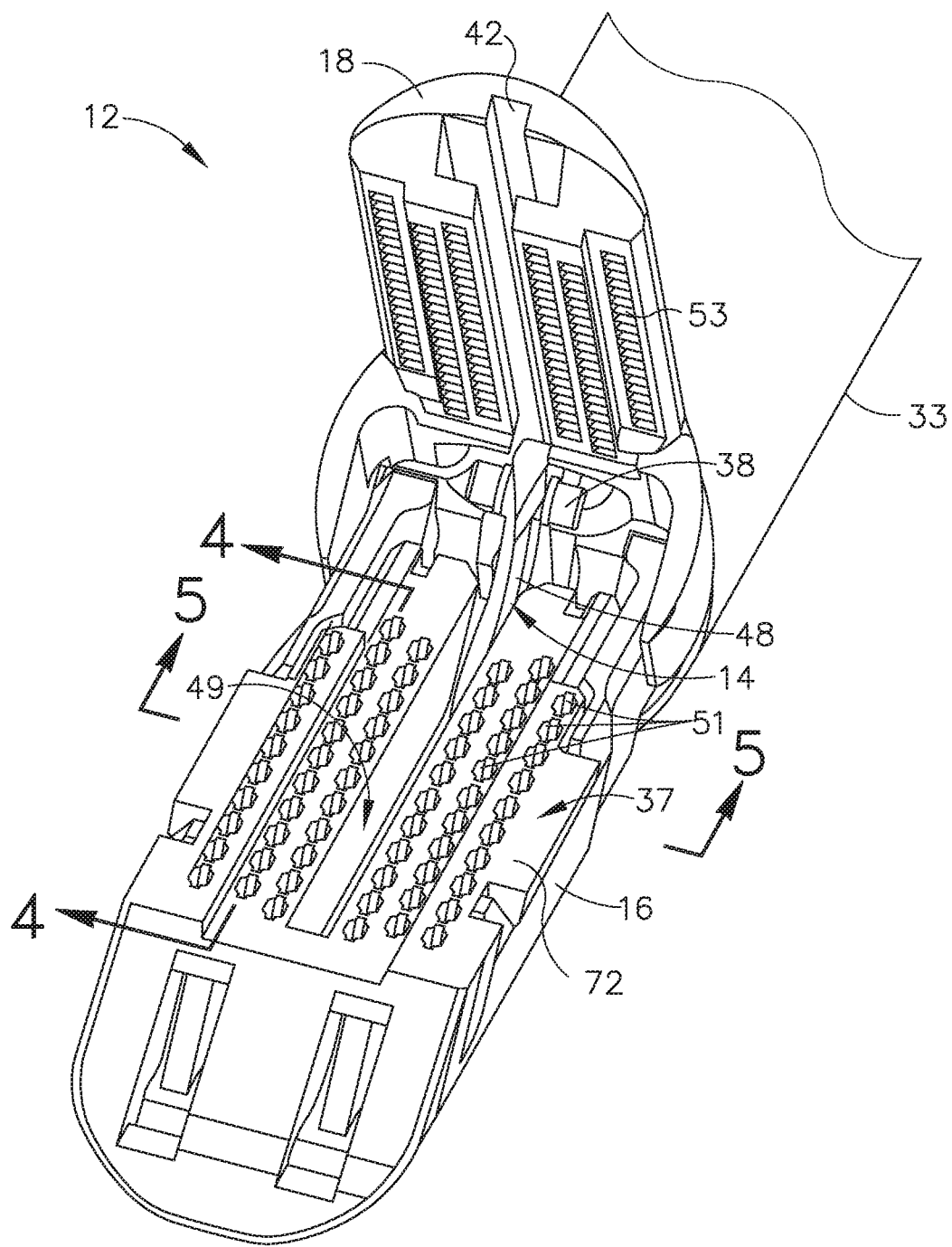
FIG. 3 depicts a perspective view of an opened end effector of the instrument of FIG. 1.
Figure 4A:
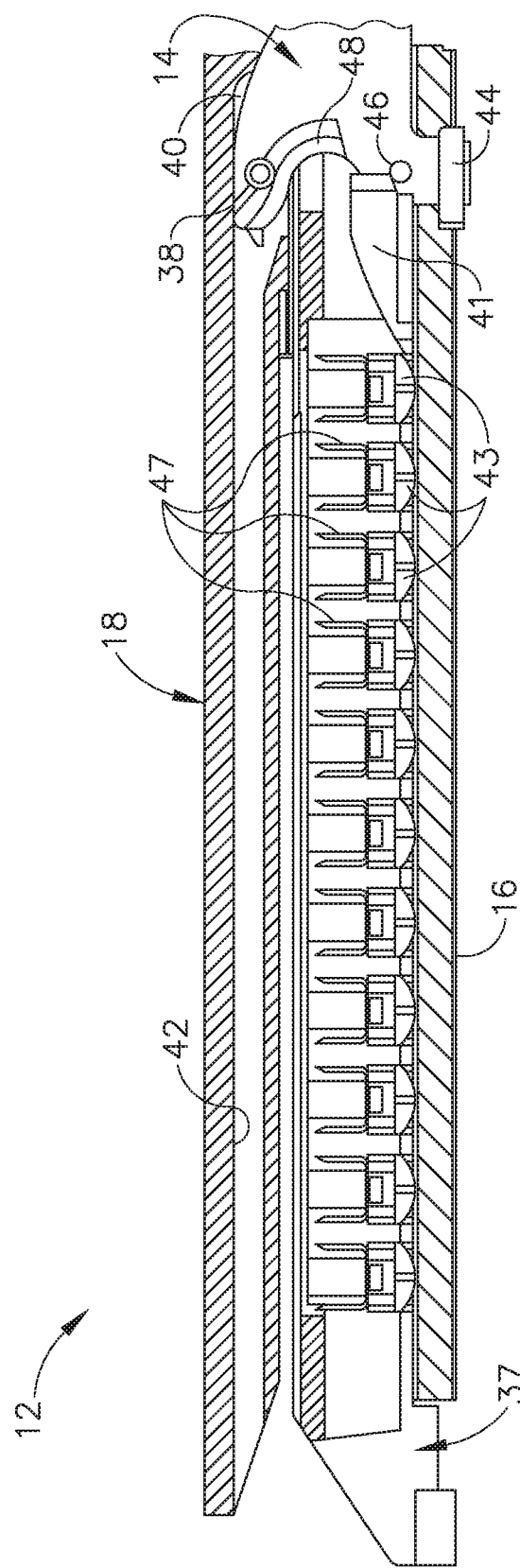
FIG. 4A depicts a side cross-sectional view of the end effector of FIG. 3, taken along line 4-4 of FIG. 3, with the firing beam in a proximal position.
Figure 4B:
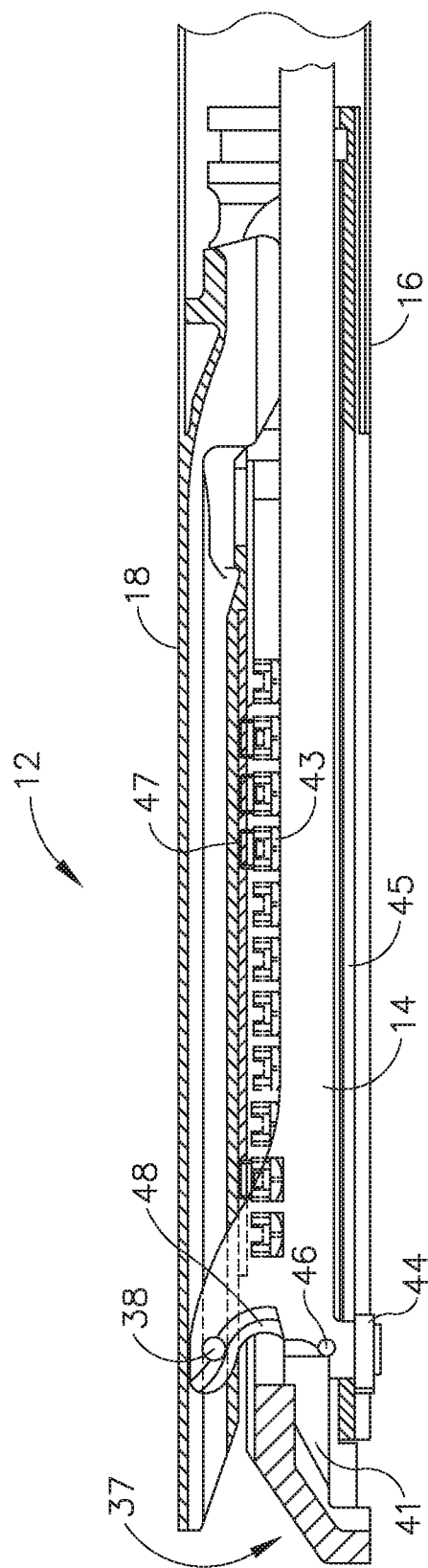
FIG. 4B depicts a side cross-sectional view of the end effector of FIG. 3, taken along line 4-4 of FIG. 3, with the firing beam in a distal position.
Figure 5:
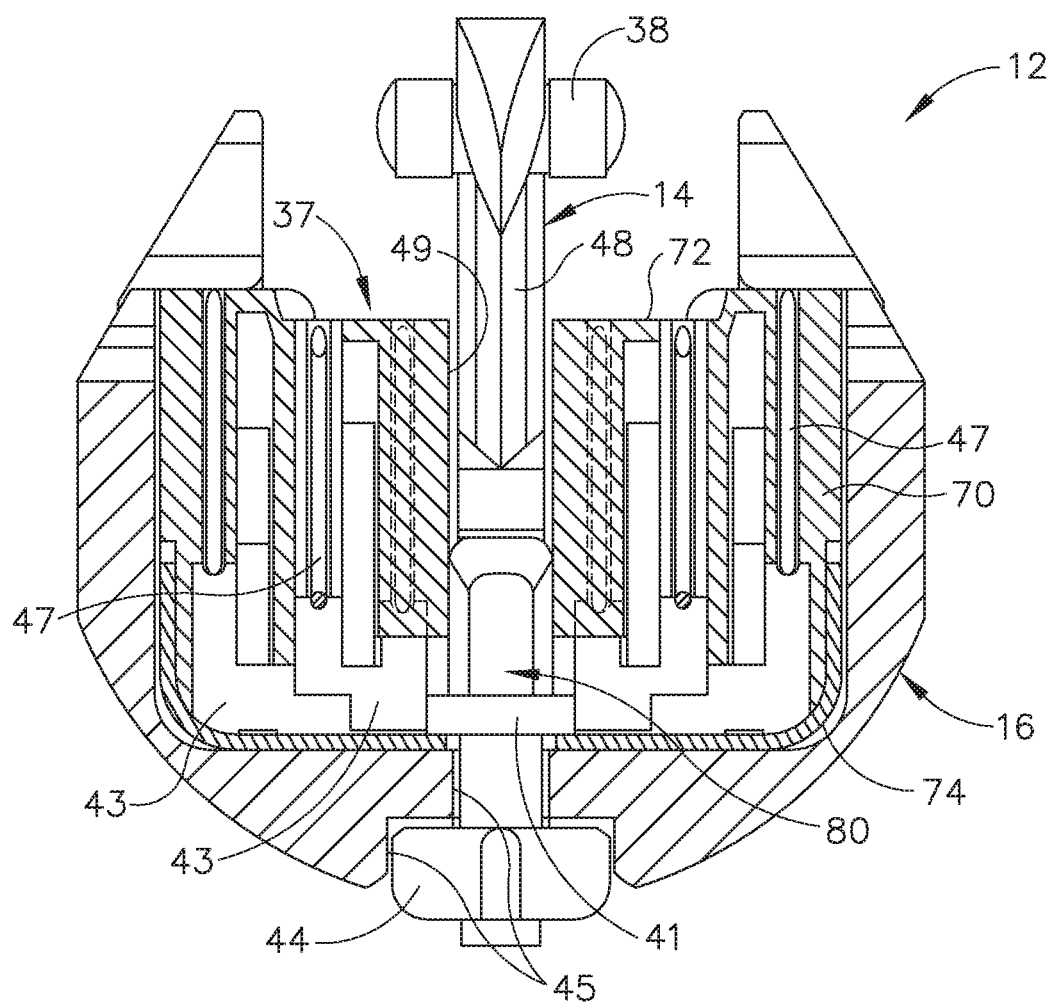
FIG. 5 depicts an end cross-sectional view of the end effector of FIG. 3, taken along line 5-5 of FIG. 3.
Figure 6:
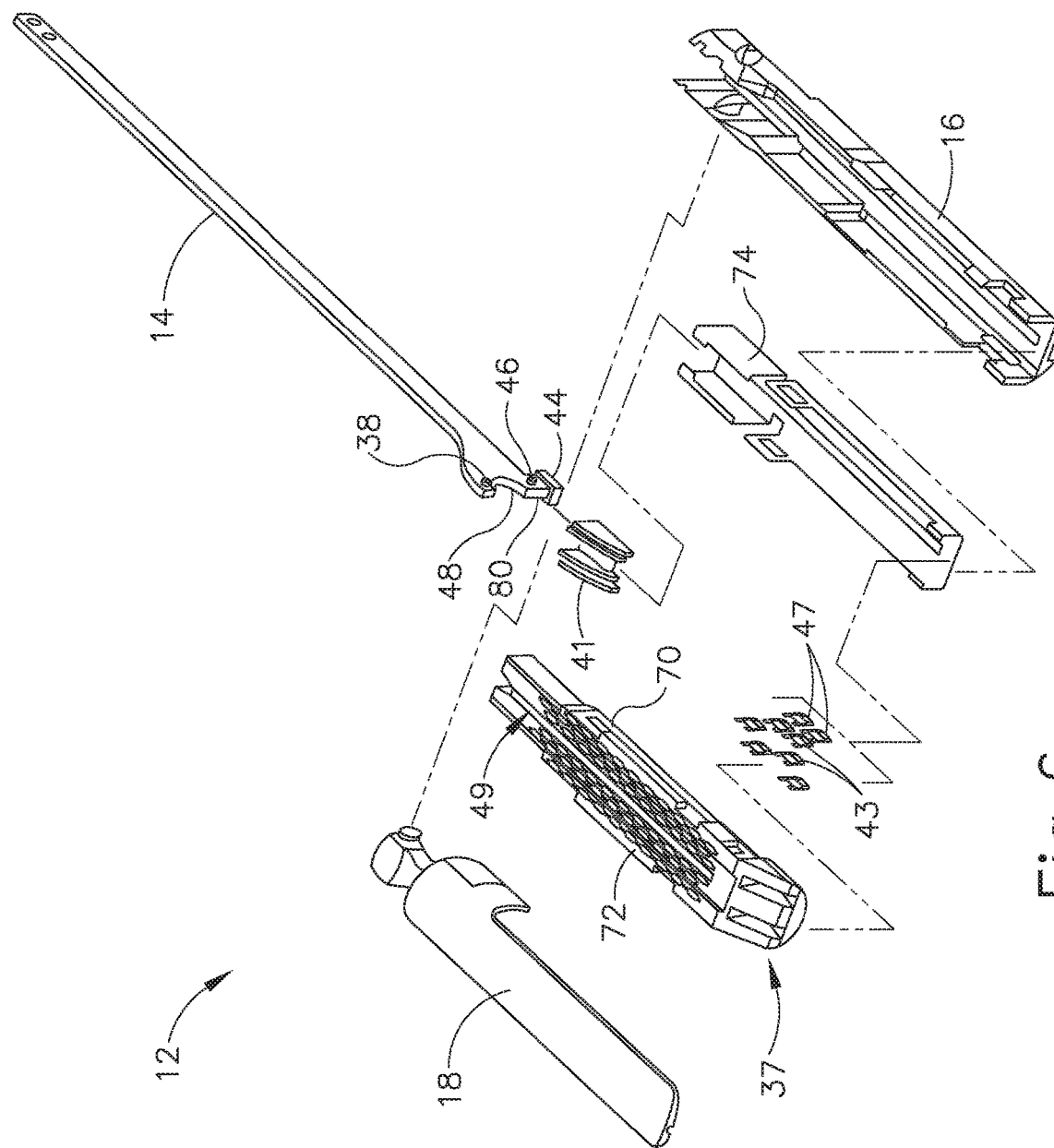
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

Various exemplary components, configurations, and operabilities that may be incorporated into staple cartridge (37) will be described in greater detail below. Staple cartridge (37) may also be constructed and operable in accordance with at least some of the teachings of U.S. Pat. No. 9,808,248, issued Nov. 7, 2017, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward caroming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
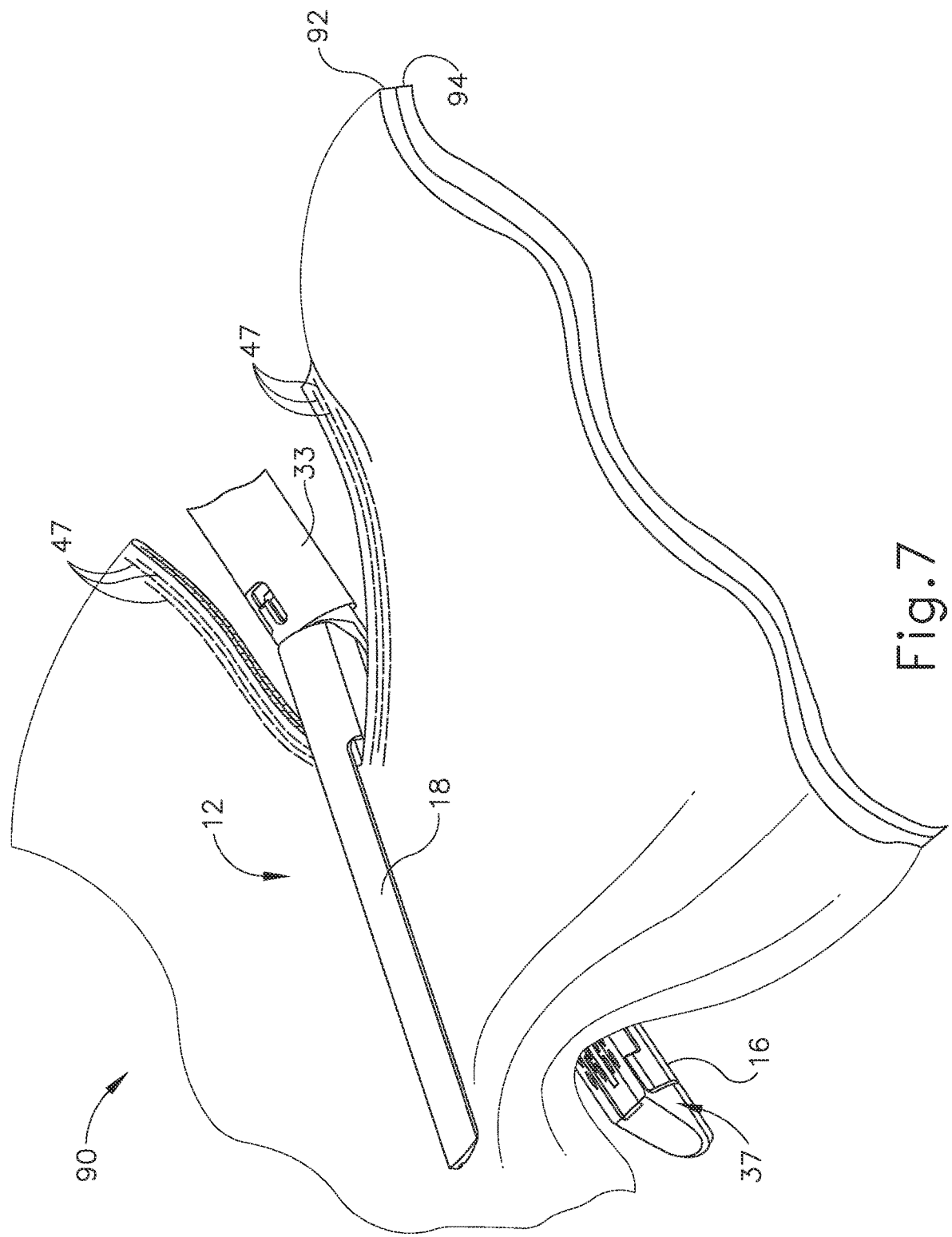
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

It should be understood that instrument (10) may be configured and operable in accordance with any of the teachings of U.S. Pat. Nos. 4,805,823; 5,415,334; 5,465,895; 5,597,107; 5,632,432; 5,673,840; 5,704,534; 5,814,055; 6,978,921; 7,000,818; 7,143,923; 7,303,108; 7,367,485; 7,380,695; 7,380,696; 7,404,508; 7,434,715; 7,721,930; U.S. Pub. No. 2010/0264193, now U.S. Pat. No. 8,408,439, issued Apr. 2, 2013; and/or U.S. Pub. No. 2012/0239012, now U.S. Pat. No. 8,453,914, issued Jun. 4, 2013. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Motorized Drive Features

Figure 8:
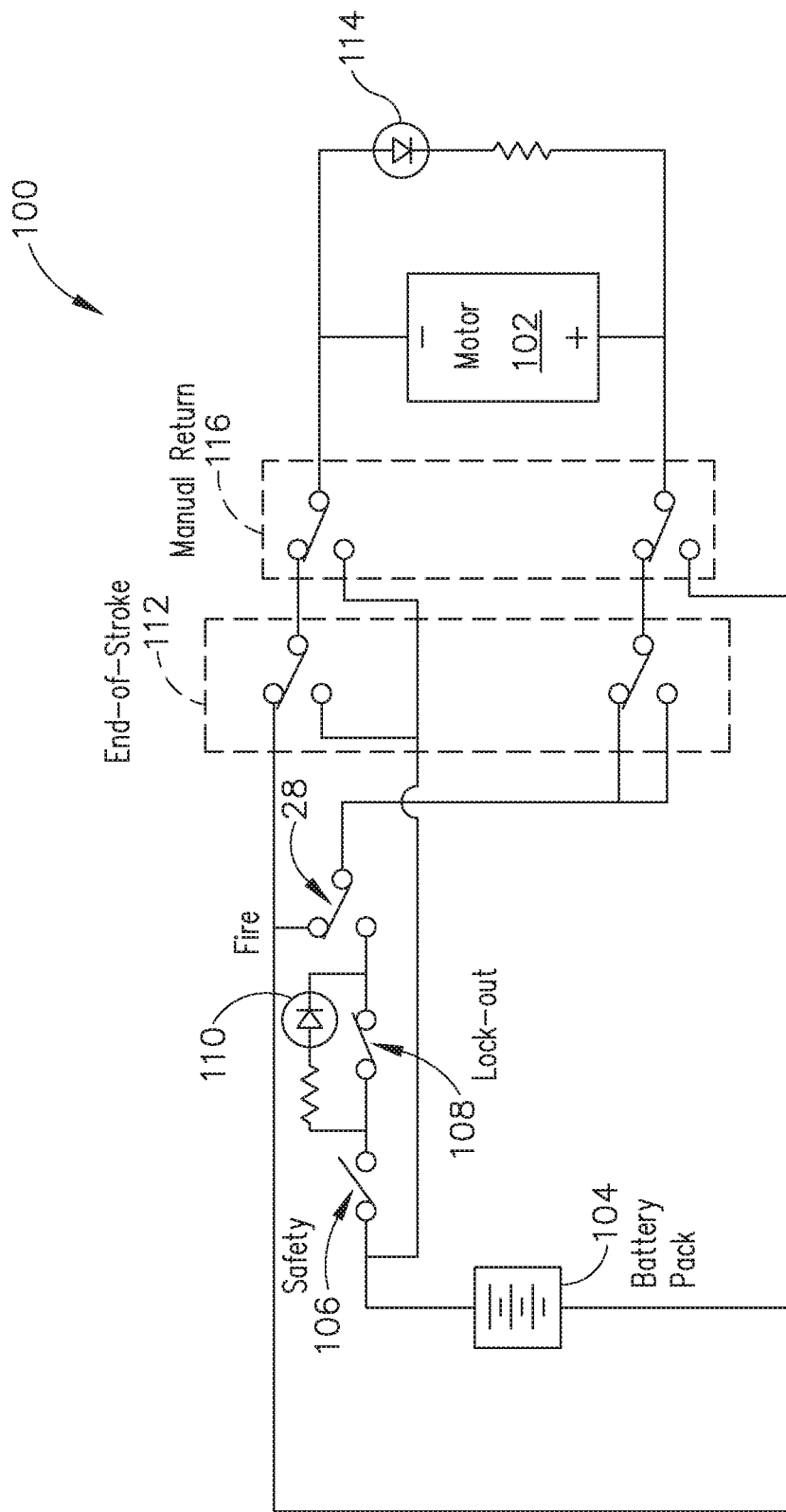
FIG. 8 depicts a schematic view of an exemplary control circuit for use in the instrument of FIG. 1.

In the present example, instrument (10) provides motorized control of firing beam (14). FIGS. 8-11 show exemplary components that may be used to provide motorized control of firing beam (14). In particular, FIG. 8 shows an exemplary control circuit (100) that may be used to power an electric motor (102) with electric power from a battery pack (104) (also shown in FIGS. 1-2). Electric motor (102) is operable to translate firing beam (14) longitudinally as will be described in greater detail below. It should be understood that the entire control circuit (100), including motor (102) and battery pack (104), may be housed within handle portion (20). FIG. 8 shows firing trigger (28) as an open switch, though it should be understood that this switch is closed when firing trigger (28) is actuated. Circuit (100) of this example also includes a safety switch (106) that must be closed in order to complete circuit (100), though it should be understood that safety switch (106) is merely optional. Safety switch (106) may be closed by actuating a separate button, slider, or other feature on handle portion (20).

Circuit (100) of the present example also includes a lockout switch (108), which is configured to be closed by default but is automatically opened in response to a lockout condition. By way of example only, a lockout condition may include one or more of the following: the absence of a cartridge (37) in lower jaw (16), the presence of a spent (e.g., previously fired) cartridge (37) in lower jaw (16), an insufficiently closed anvil (18), a determination that instrument (10) has been fired too many times, and/or any other suitable conditions. Various sensors, algorithms, and other features that may be used to detect lockout conditions will be apparent to those of ordinary skill in the art in view of the teachings herein. Similarly, other suitable kinds of lockout conditions will be apparent to those of ordinary skill in the art in view of the teachings herein. It should be understood that circuit (100) is opened and thus motor (102) is inoperable when lockout switch (108) is opened. A lockout indicator (110) (e.g., an LED, etc.) is operable to provide a visual indication of the status of lockout switch (108). By way of example only, lockout switch (108), lockout indicator (110), and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Once firing beam (14) reaches a distal-most position (e.g., at the end of a cutting stroke), an end-of-stroke switch (112) is automatically switched to a closed position, reversing the polarity of the voltage applied to motor (102). This reverses the direction of rotation of motor (102), it being understood that the operator will have released firing trigger (28) at this stage of operation. In this operational state, current flows through a reverse direction indicator (114) (e.g., an LED, etc.) to provide a visual indication to the operator that motor (102) rotation has been reversed. Various suitable ways in which end-of-stroke switch (112) may be automatically switched to a closed position when firing beam (14) reaches a distal-most position will be apparent to those of ordinary skill in the art in view of the teachings herein. Similarly, various suitable forms that reverse direction indicator (114) may take will be apparent to those of ordinary skill in the art in view of the teachings herein.

Handle portion (20) of the present example also includes a manual return switch (116), which is also shown in circuit (100). Manual return switch (116) is configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide functionality similar to end-of-stroke switch (112), reversing the polarity of the voltage applied to motor (102) to thereby reverse the direction of rotation of motor (102). Again, this reversal may be visually indicated through reverse direction indicator (114).

In some versions, one or more of switches (28, 106, 108, 112, 116) are in the form of microswitches. Other suitable forms will be apparent to those of ordinary skill in the art in view of the teachings herein. In addition to or in lieu of the foregoing, at least part of circuit (100) may be configured in accordance with at least some of the teachings of U.S. Pat. No. 8,210,411, entitled "Motor-Driven Surgical Instrument," issued Jul. 3, 2012, the disclosure of which is incorporated by reference herein.

Figure 9:
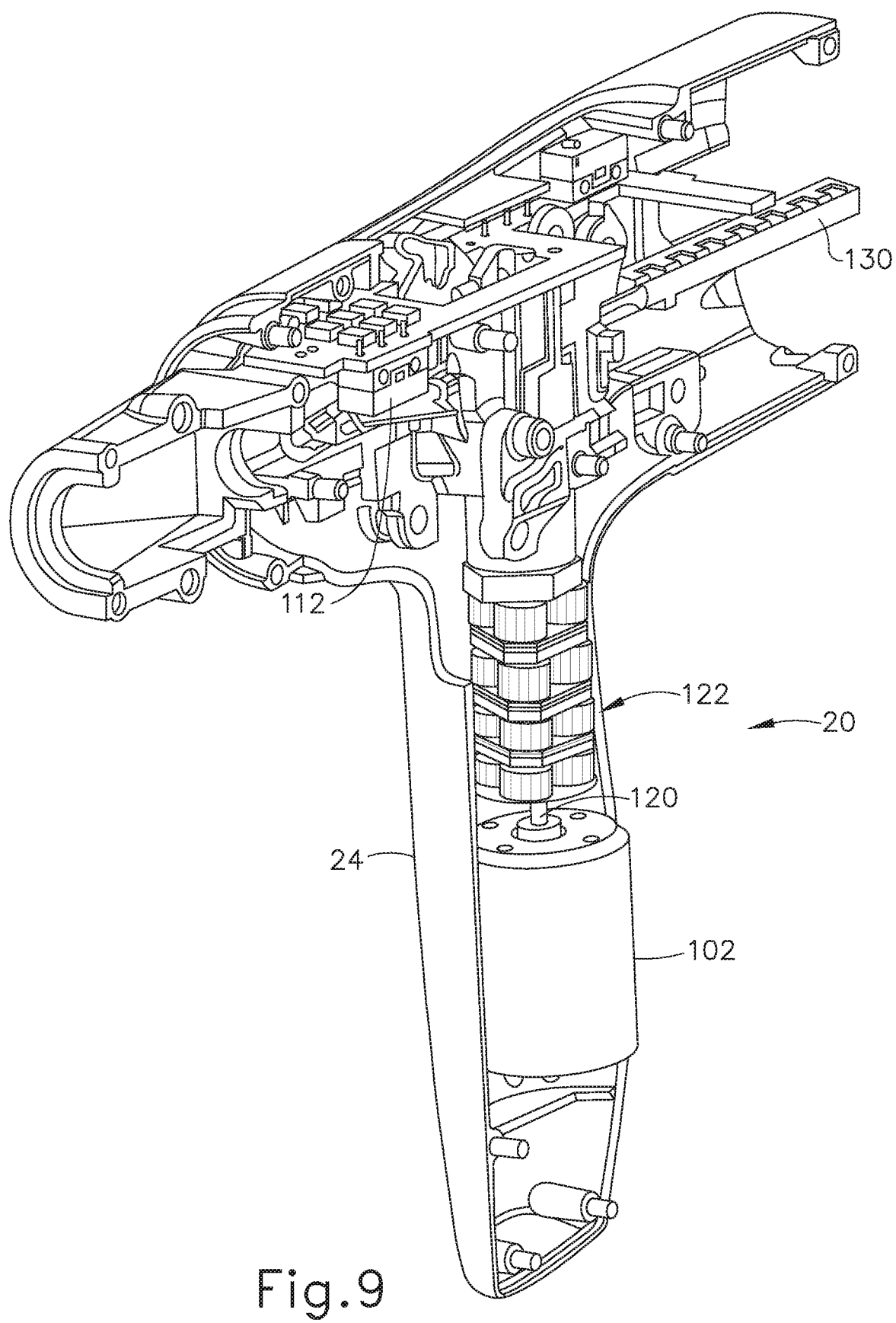
FIG. 9 depicts a perspective view of the handle assembly of the instrument of FIG. 1, with a housing half removed.
Figure 10:
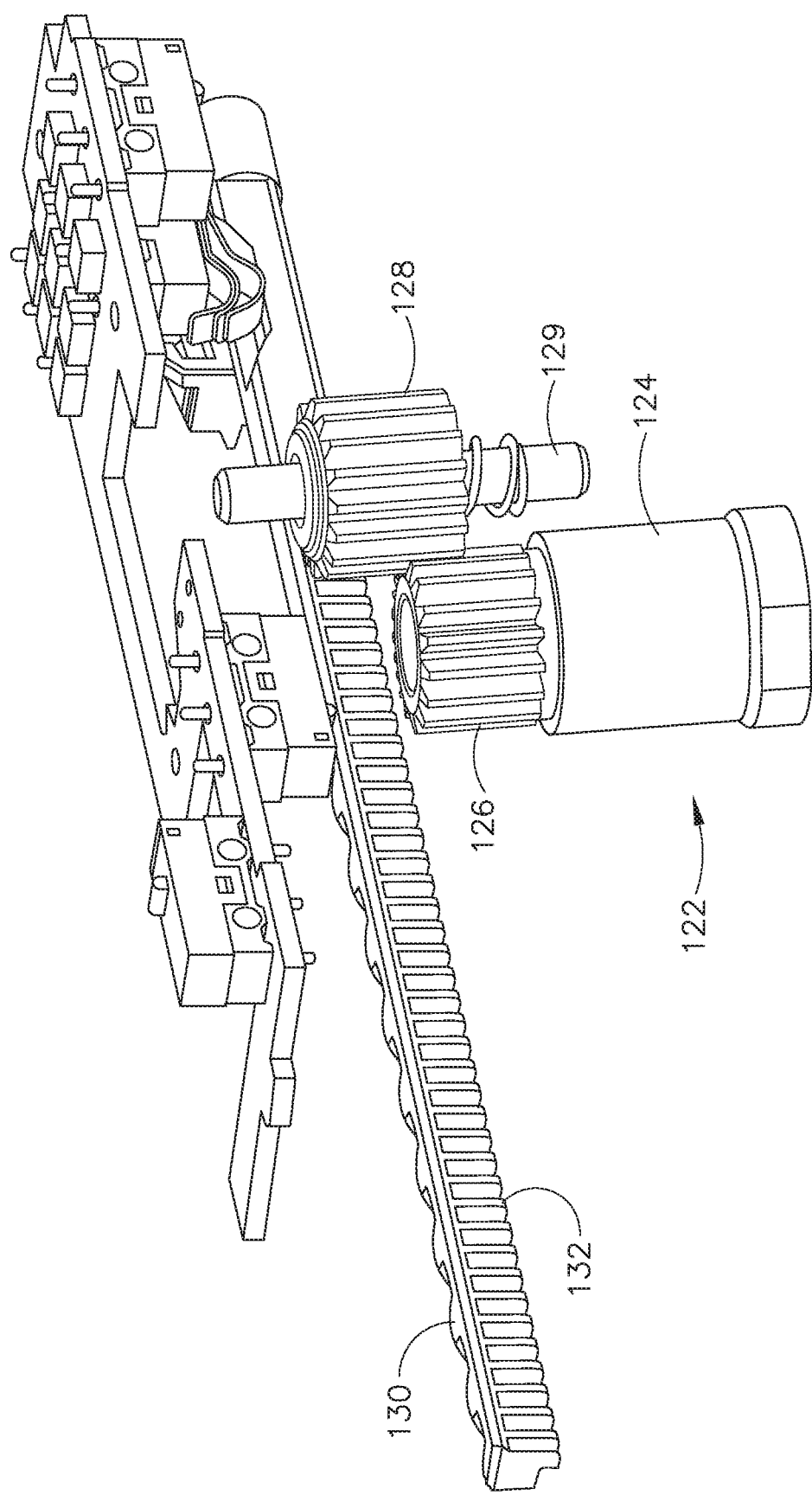
FIG. 10 depicts a perspective view of drive assembly components from the handle assembly of FIG. 9.
Figure 11:
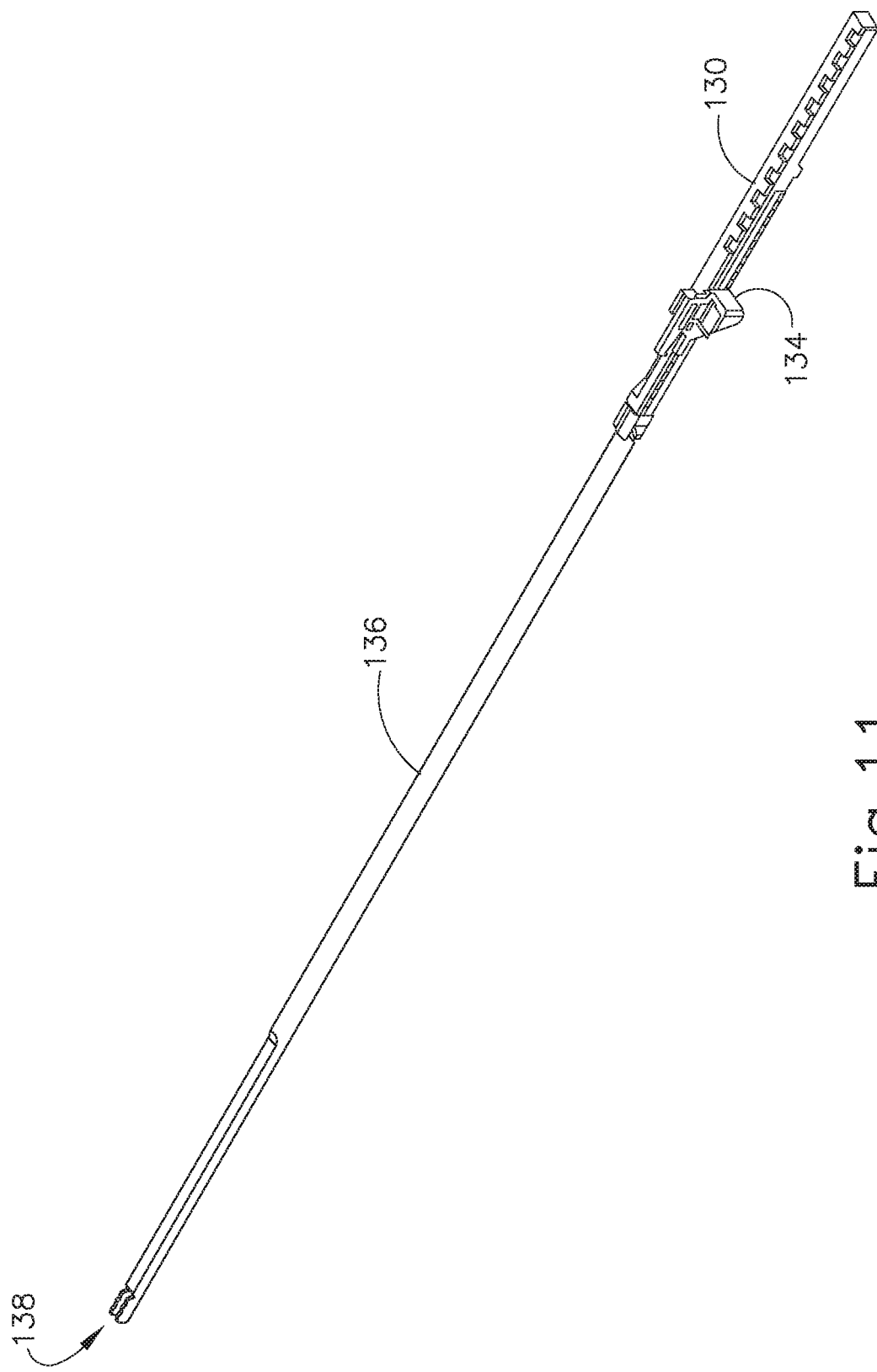
FIG. 11 depicts a perspective view of an elongate member from the drive assembly of FIG. 10.

FIGS. 9-11 show various mechanical components that may be used to provide motorized translation of firing beam (14). In particular, FIG. 9 shows motor (102) housed in pistol grip (24) of handle portion (20). It should be understood that battery pack (104) (shown in FIGS. 1-2) may also be located in pistol grip (24) (e.g., below motor (102)) and/or elsewhere within handle portion (20). Motor (102) has a drive shaft (120) that is coupled with a gear assembly (122). Gear assembly (122) has an external casing (not shown) and is operable to drive an upper gear (126), which is shown in FIG. 10. Upper gear (126) meshes with a pinion (128), which is rotatably supported by a pin (129) secured in handle portion (20). It should therefore be understood that activation of motor (102) will ultimately rotate pinion (128) within handle portion (20).

As also shown in FIGS. 9-10, a translating rack (130) includes teeth (132) that mesh with pinion (128), such that rack (130) translates longitudinally when pinion (128) rotates. As shown in FIG. 11, rack (130) is coupled with an elongate member (136), which extends through shaft (22) and includes a distal end (138) that couples with the proximal end of firing beam (14). Elongate member (136) translates within shaft (22), such that elongate member (136) communicates longitudinal motion of rack (130) to firing beam (14). It should therefore be understood that activation of motor (102) will ultimately translate firing beam (14) within end effector (12). In particular, motor (102) may drive firing beam (14) distally to sever tissue (90) and drive staples (47) into tissue (90). A switch actuation arm (134) extends laterally from rack (130), and is positioned to engage end-of-stroke switch (112) when firing beam (14) reaches a distal-most position (e.g., after tissue (90) has been severed and staples (47) have been driven into tissue (90)). As noted above, this engagement of end-of-stroke switch (112) automatically reverses motor (102) to return firing beam (14) from the distal-most position to the proximal position, enabling anvil (18) to be pivoted away from lower jaw (16) to release tissue (90).

Use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

In addition to or in lieu of the foregoing, the features operable to drive firing beam (14) may be configured in accordance with at least some of the teachings of U.S. Pub. No. 2012/0239012, now U.S. Pat. No. 8,453,914, issued Jun. 4, 2013, the disclosure of which is incorporated by reference herein; and/or in accordance with at least some of the teachings of U.S. Pub. No. 2012/0239012, now U.S. Pat. No. 8,453,914, issued Jun. 4, 2013 the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

III. Exemplary End Effector with Stabilization Features

In some instances it may be desirable to provide a mechanism for ensuring that anvil (18) has clamped squarely against cartridge (37) and at an appropriate height relative to cartridge (37) prior to firing staples (47) into tissue (90). For instance, in the event that anvil (18) and cartridge (37) clamp against tissue that might be unusually thick in one area, and thinner in another, it may be desirable to align anvil (18) against cartridge (37) even with uneven tissue clamped therebetween. Upon clamping tissue, it may also be desirable to prevent lateral rolling and/or lateral pivoting deflection of anvil (18) relative to cartridge (37).

Figure 12:
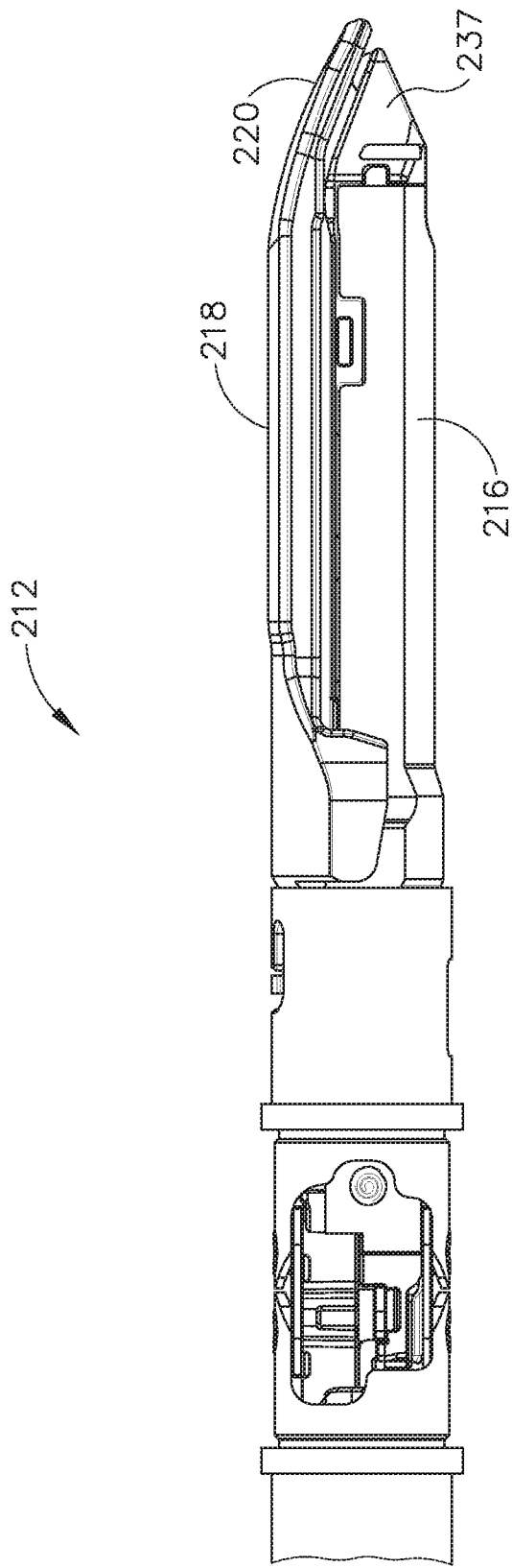
FIG. 12 depicts a side, elevation view of an exemplary alternative version of an end effector suitable for incorporation in the instrument of FIG. 1.

FIG. 12 shows an exemplary end effector (212) operable for use with an instrument such as instrument (10) shown in FIG. 1. For instance, end effector (212) may be used in place of end effector (12). It will be appreciated that end effector (212) may be integrally formed with articulation mechanism (11) or may be separately formed and removably connected to articulation mechanism (11). Other suitable variations will be apparent to one of ordinary skill in the art in view of the teachings herein. End effector (212) comprises an anvil (218) and lower jaw (216). Lower jaw (216) is operable to hold staple cartridge (237). In general, anvil (218) clamps against cartridge (237) to clamp tissue therebetween. Thereafter, staples within cartridge (237) may be fired into tissue and anchored in the tissue as a result of staples bending against anvil (218). With respect to clamping tissue and firing staples, end effector (212) is substantially similar to end effector (12) of FIG. 1. As anvil (218) contacts cartridge (237), features that will be discussed in further below may be used to laterally stabilize anvil (218). As a result, staples (such as staples (47)) may be fired from cartridge (237) through tissue and against anvil (218) without anvil (218) tipping laterally relative to cartridge (237).

Figure 13:
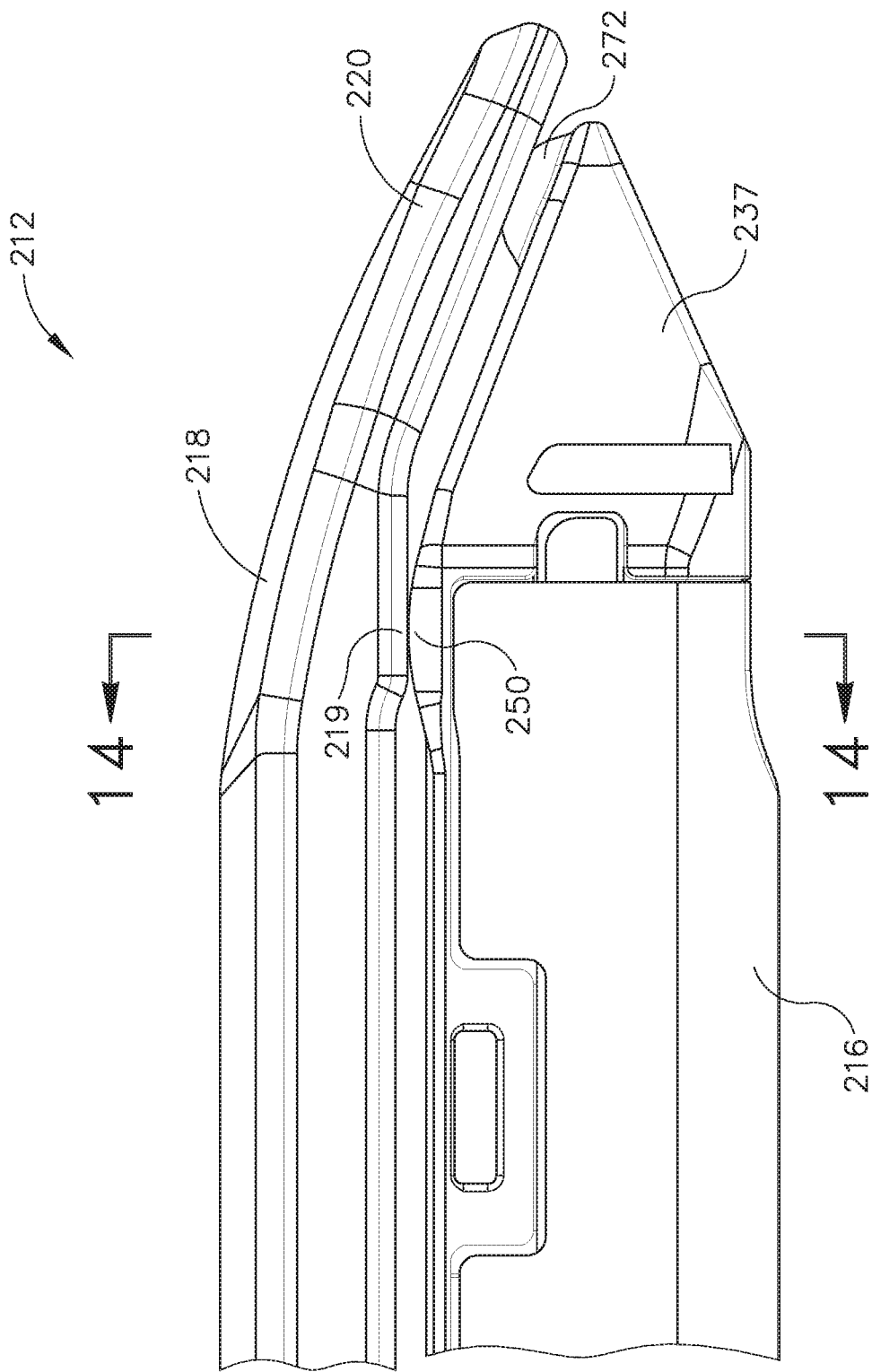
FIG. 13 depicts an enlarged, side view of the end effector of FIG. 12 showing laterally separated, upwardly extending protrusions.
Figure 14:
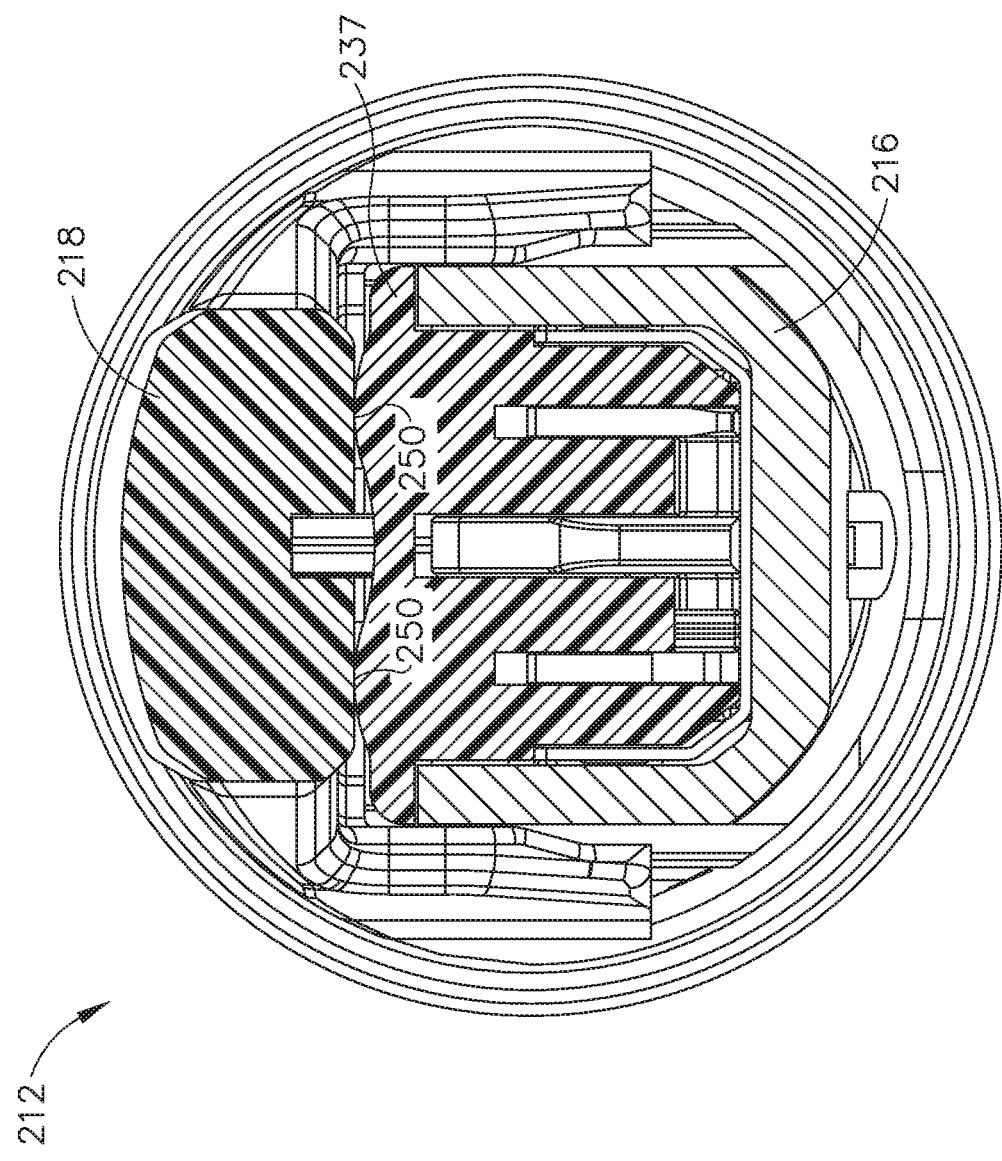
FIG. 14 depicts a cross sectional view of the end effector of FIG. 12 taken along line 14-14 of FIG. 13 showing the lateral protrusions.

FIG. 13 shows an enlarged view of end effector (212). Cartridge (237) comprises a plurality of laterally separated, upwardly extending protrusions (250). As seen in FIG. 14, lateral protrusions (250) comprise two laterally spaced apart protrusions (250). Protrusions (250) are spaced apart such that when anvil (218) closes upon cartridge (237), anvil (218) does not rock laterally in relation to cartridge (237). In the illustrated version, protrusions (250) have a shallow, rounded shape though it will be understood that any suitable shape for protrusions (250) may be used as would be apparent to one of ordinary skill in the art in view of the teachings herein. For instance, protrusions (250) may have a pointed or raised plateau shape. In some versions, protrusions (250) could be positioned along the length of cartridge (237).

Figure 15:
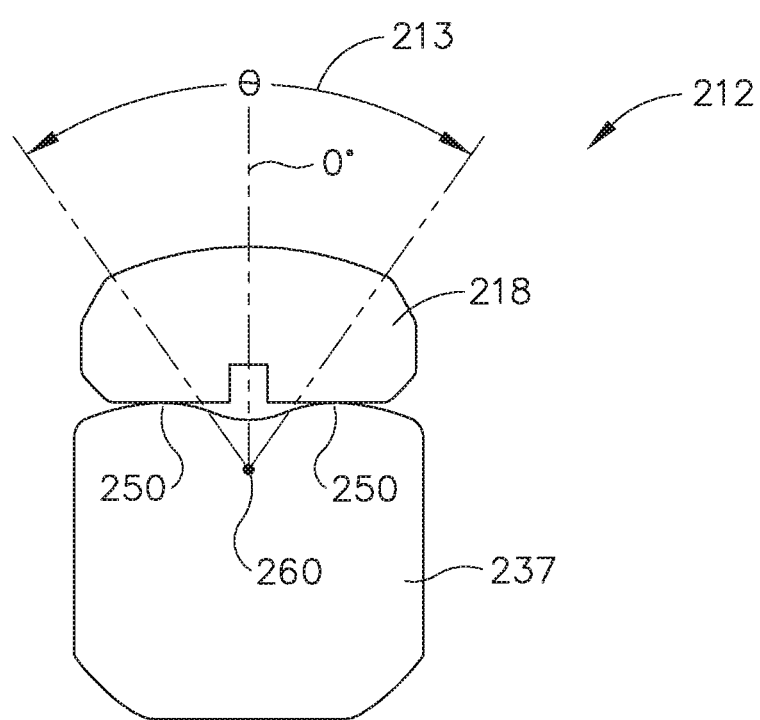
FIG. 15 depicts a diagrammatic end view of the end effector of FIG. 12 showing the lateral roll angle of the anvil.

FIG. 15 depicts a diagrammatic end view of end effector (212) illustrating a roll angle θ (213) of anvil (218) relative to a longitudinal axis (260) that extends through the center of end effector (212). It will be appreciated that roll angle θ (213) represents a lateral roll either positive or negative from the 0° angle in the event that tissue (90) causes anvil (218) to roll while clamping against cartridge (237). Lateral protrusions (250) are operable to provide two points of contact between anvil (218) and cartridge (237) such that roll angle θ (213) of anvil (218) remains approximately near 0° when anvil (218) contacts lateral protrusions (250). It will be understood that due to clamping tissue between anvil (218) and cartridge (237), roll angle θ (213) may deviate from 0° but only slightly due to the dual contact points provided by protrusions (250). In other words, as anvil (218) closes upon cartridge (237), anvil (218) may laterally roll during the motion of closing upon cartridge (237); however, the contact between anvil (218) and protrusions (250) is operable to correct any lateral rolling of anvil (218). As a result, staple forming pockets (253) (seen in FIG. 16) align with apertures (251) (seen in FIG. 17) prior to firing staples. Furthermore, protrusions (250) consistently establish where the preload from anvil (218) will be applied against the upper deck of cartridge (237). While the exemplary version shows protrusions (250) located on cartridge (237), it will be understood that in addition or in the alternative, protrusions (250) may be positioned on anvil (218). Other suitable positions for protrusions (250) for laterally stabilizing anvil (218) will be apparent to one of ordinary skill in the art in view of the teachings herein. FIG. 13 further shows anvil (218) having a protrusion (219) operable to engage protrusions (250), thereby promoting further contact between cartridge (237) and anvil (218). Protrusion (219) is shaped as a generally planar surface though other suitable shapes may be used as would apparent to one of ordinary skill in the art in view of the teachings herein. Protrusion (219) can also be seen in FIG. 16.

It will also be appreciated that in some instances, as anvil (218) closes against cartridge (237) it may be desirable to prevent or correct lateral pivoting deflection of anvil (218) relative to cartridge (237).

Figure 16:
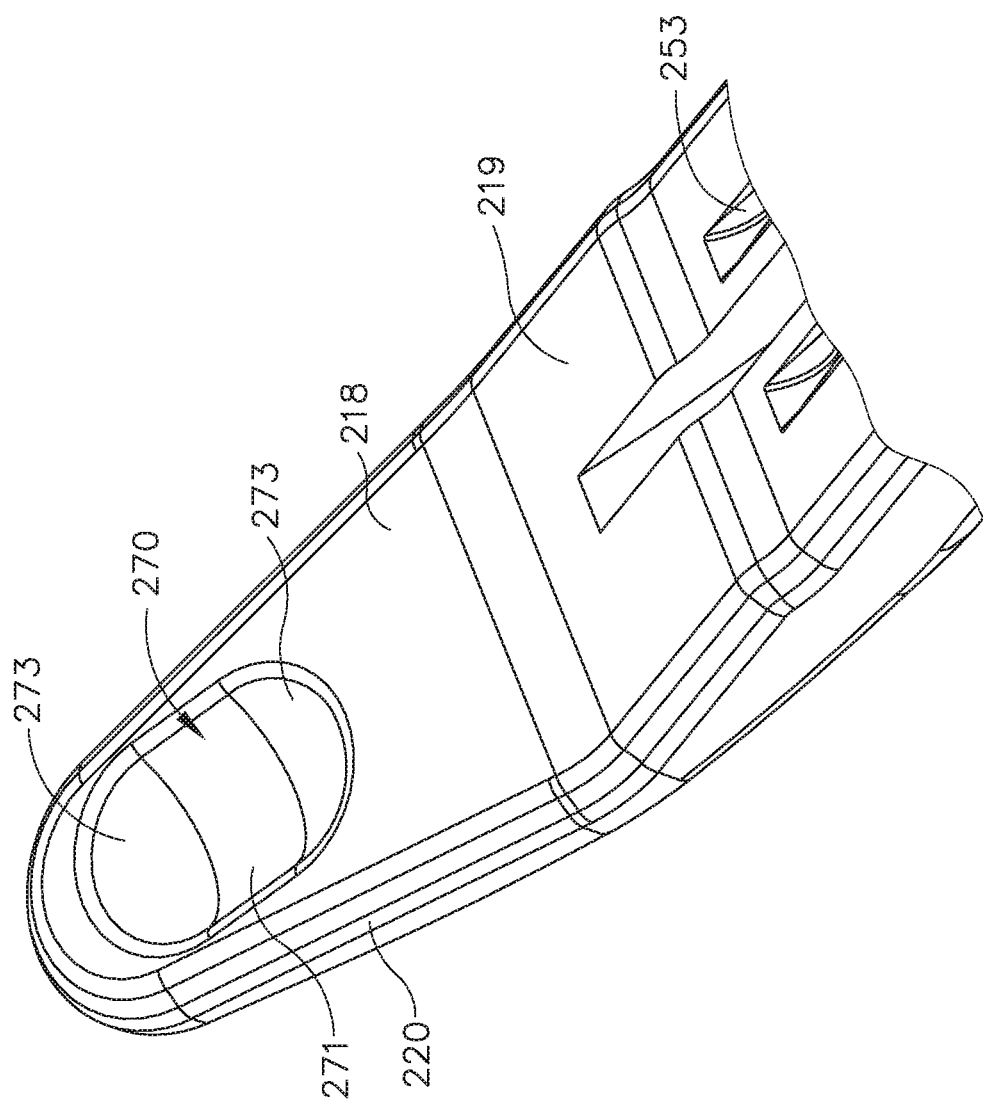
FIG. 16 depicts an enlarged, perspective view of the anvil of FIG. 12 with an engagement groove.

FIG. 16 shows an underside view of anvil (218) showing an engagement groove (270). Engagement groove (270) is shaped as an elongated semi-spherical groove within anvil (218), though it will be understood that engagement groove (270) may have any suitable shape for receiving a protrusion (272) (shown in FIG. 17), which will be discussed in more detail below. Groove (270) in the illustrated version comprises a straight curved portion (271) and spherical curved portions (273) flanking the straight curved portion to form groove (270). Groove (270) of the exemplary version is laterally centered along anvil (218) though other suitable positions for groove (270) may be used. In the illustrated version, engagement groove (270) is positioned such that engagement groove (270) and protrusions (250) form a generally triangular shape when anvil (218) is closed against cartridge (237). Of course, this configuration is just a merely illustrative example, and these features could be subject to various suitable alternative arrangements. Anvil (218) is shaped to laterally taper toward engagement groove (270) in the present example, though any suitable shape for anvil (218) may be used as would be apparent to one of ordinary skill in the art in view of the teachings herein.

Figure 17:
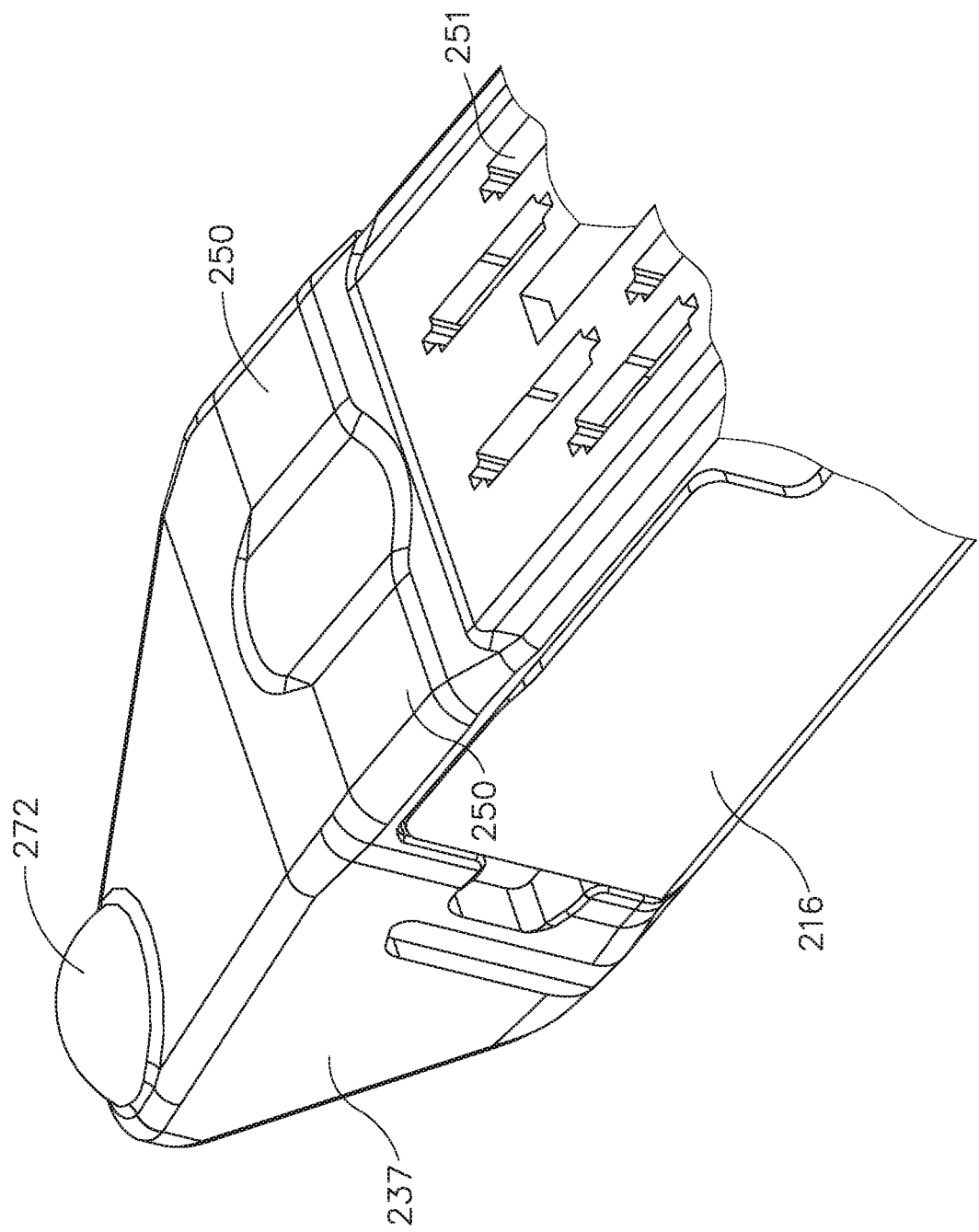
FIG. 17 depicts an enlarged, perspective view of the cartridge of FIG. 12 with a protrusion and laterally separated, upwardly extending protrusions.

FIG. 17 shows cartridge (237) of end effector (212) with a protrusion (272). It will be appreciated that when anvil (218) closes against cartridge (237), protrusion (272) fits within engagement groove (270). In particular, protrusion (272) may first contact spherical curved portion (273) and slide to straight curved portion (271) as anvil (218) presses towards cartridge (237). It will be appreciated that engagement groove (270) is sized larger than protrusion (272). As a result, protrusion (272) need not necessarily be perfectly aligned with engagement groove (270) for engagement groove (270) to catch protrusion (272). Cartridge (237) of the exemplary version laterally and vertically tapers towards protrusion (272) to form a narrowed tip, though it will be understood that any suitable shape for cartridge (237) may be used as would be apparent to one of ordinary skill in the art in view of the teachings herein.

Protrusion (272) is operable to catch a portion of engagement groove (270) such as spherical curved portion (273) where thereafter, the curved contour of engagement groove (270) enables protrusion (272) to slide into a more central portion of engagement groove (270) such as straight curved portion (271) thereby providing a fit between protrusion (272) and engagement groove (270). Once protrusion (272) and engagement groove (270) fully engage each other, it will be appreciated that anvil (218) cannot deflect laterally relative to cartridge (237). For instance, in the exemplary version, the width of engagement groove (270) complements the diameter of protrusion (272) thereby preventing deflection of anvil (218) and promoting anvil (218) and cartridge (237) alignment. However, the length of engagement groove (270) is longer than the diameter of protrusion (272) thereby promoting engagement of protrusion (272) and engagement groove (270) and furthermore promoting sliding of protrusion (272) into straight curved portion (271) of engagement groove (270). It will further be understood that if anvil (218) is laterally pivotally deflected during closure, engagement groove (270) and protrusion (272) cooperate to guide anvil (218) into alignment.

Figure 18:
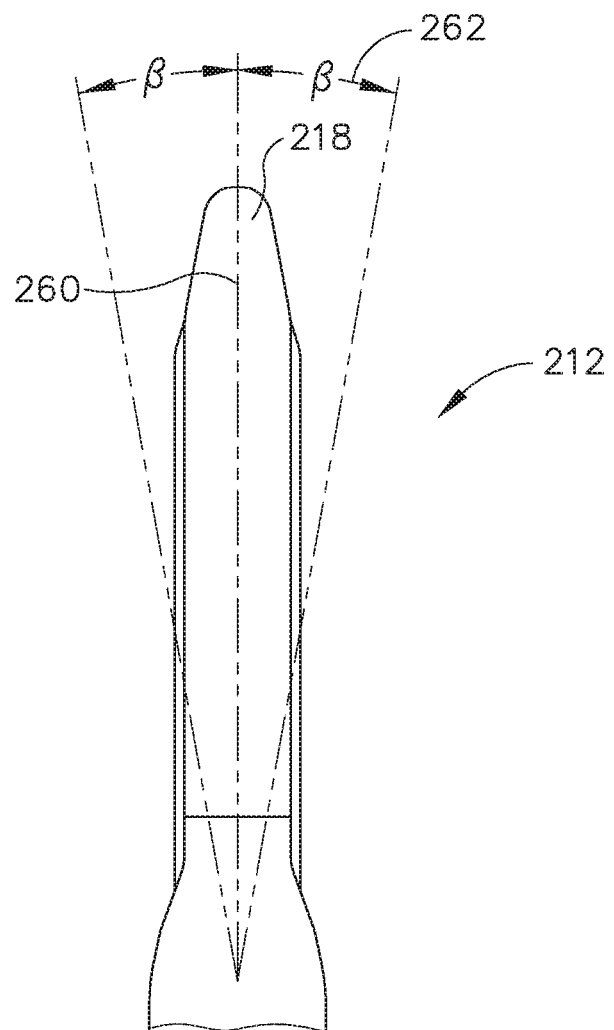
FIG. 18 depicts a top, diagrammatic view of the end effector of FIG. 12 showing the angle of deflection of the anvil.

FIG. 18 shows longitudinal axis (260) extending through the center of end effector (212). An angle of deflection β (262) represents the amount of deflection to the left or right of longitudinal axis (260) anvil (218) could experience in some scenarios during use. For instance, deflection of anvil (218) could occur in the event that thick or particularly dense tissue is positioned between anvil (218) and cartridge (237) as anvil (218) clamps against cartridge (237) or when the density and/or thickness of tissue in the area between anvil (218) and lower jaw (216) varies across the width of anvil (218) and lower jaw (216). Of course, as discussed above, it will be appreciated that by engaging engagement groove (270) with protrusion (272), anvil (218) resists deflecting, thereby keeping angle of deflections β (262) at approximately 0° relative to longitudinal axis (260). It will be understood that in some circumstances, slight deflection could occur, but generally speaking, protrusion (272) and engagement groove (270) help maintain angle of deflection β (262) at or near 0° relative to longitudinal axis (260).

Furthermore, as can be seen in FIG. 16, anvil (218) has an anvil tip (220) where anvil tip (220) has a bent, sloped shape angled toward cartridge (237). It will be appreciated that the bent shape of anvil tip (220) complements the shape of cartridge (237) such that anvil (218) further resists deflecting relative to cartridge (237). While the exemplary version depicts anvil tip (220) having a bent shape, it will be understood that anvil tip (220) need not necessarily have a bent shape and engagement groove (270) and protrusion (272) may be used in situations where anvil tip (220) is oriented in a straight manner relative to the rest of anvil (218). Indeed engagement groove (270) and protrusion (272) may also be used in conjunction with cartridges (237) that might be straight rather than having an angled tip as seen, for instance, in FIG. 12.

Figure 19:
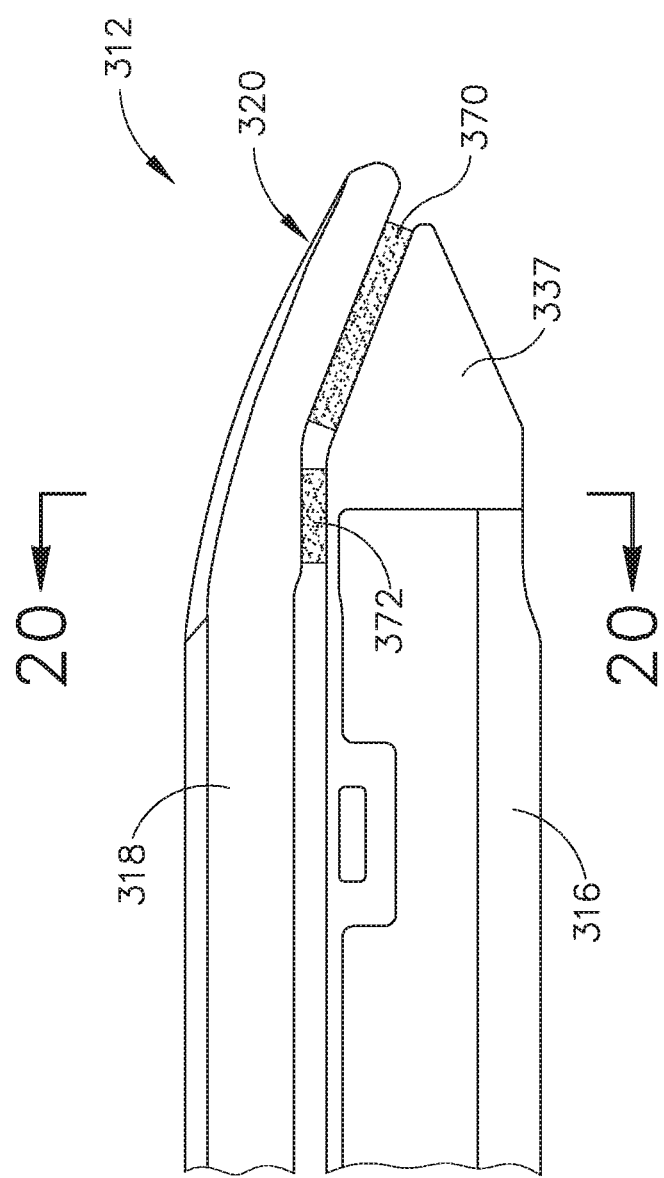
FIG. 19 depicts a side, elevation view of an alternative exemplary version of an end effector with an alignment member and lateral stabilization members.

FIG. 19 depicts an alternative exemplary version of an end effector (312). It will be appreciated that end effector (312) may be used interchangeably with or in place of end effector (12, 212) as seen in FIGS. 1 and 12. End effector (312) comprises an anvil (318) and lower jaw (316). Lower jaw (316) is in communication with a cartridge (337) operable to hold a plurality of staples in a substantially similar manner relative to the lower jaw (16) and cartridge (37) shown in FIG. 3. Anvil tip (320) is bent to generally complement the shape of cartridge (237) though it will be understood that anvil tip (320) may have other suitable shapes.

End effector (312) further comprises a distally positioned anvil alignment member (370) and a lateral stabilization member (372). It will be appreciated that alignment member (370) is operable to define spacing between anvil (318) and cartridge (337) at the distal end of end effector (312). Furthermore, lateral stabilization member (372) is operable to laterally stabilize anvil (318) against cartridge (337), which will be described in further detail below.

Alignment member (370) of the present example has a wedge shape with a triangular cross section. It will be understood that the triangular wedge shape of alignment member (370) is configured to complement the contour of anvil (318) and cartridge (337). For instance, in some instances, it may be desirable to maintain a particular distance between anvil (318) and cartridge (337) based on the type and/or thickness of tissue being placed between anvil (318) and cartridge (337). Alignment member (370) may thus be positioned between a portion of anvil (318) and cartridge (337) to prevent anvil (318) from closing against cartridge (337) further than what might be desired by the user. Furthermore, not only does alignment member (370) prevent further closure of anvil (318) against cartridge (337), alignment member (370) allows anvil (318) to maintain a specific distance from cartridge (337). Yet further, alignment member (370) fills the space between anvil (318) and cartridge (337) such that the distal end of anvil (318) and cartridge (337) with alignment member (370) placed in between forms an atraumatic blunt end that may be used to urge end effector (312) through tissue without either anvil (318) or cartridge (337) inadvertently catching on tissue. In the exemplary version, anvil (318) and cartridge (337) have a planar profile where anvil (318) and cartridge (337) meet alignment member (370). However, it will be appreciated that anvil (318) and cartridge (337) may have other suitable shapes as would be apparent to one of ordinary skill in the art in view of the teachings herein. Accordingly, alignment member (370) may also have any suitable shape to complement anvil (318) and cartridge (337). It will be appreciated that in some versions, alignment member (370) may be removable in relation to either anvil (318) or cartridge (337) or may be integrally formed with either anvil (318) or cartridge (337). In yet other exemplary versions, it will be appreciated that alignment member (370) may be split such that a portion is connected to anvil (318) where another portion is connected to cartridge (337). In some instances, end effector (312) may be provided with a plurality of modular alignment members (370) having different shapes and sizes such that the user could, for instance, use one shape for alignment member (370) in one type of tissue and another shape or size alignment member (370) in another type of tissue.

Figure 20:
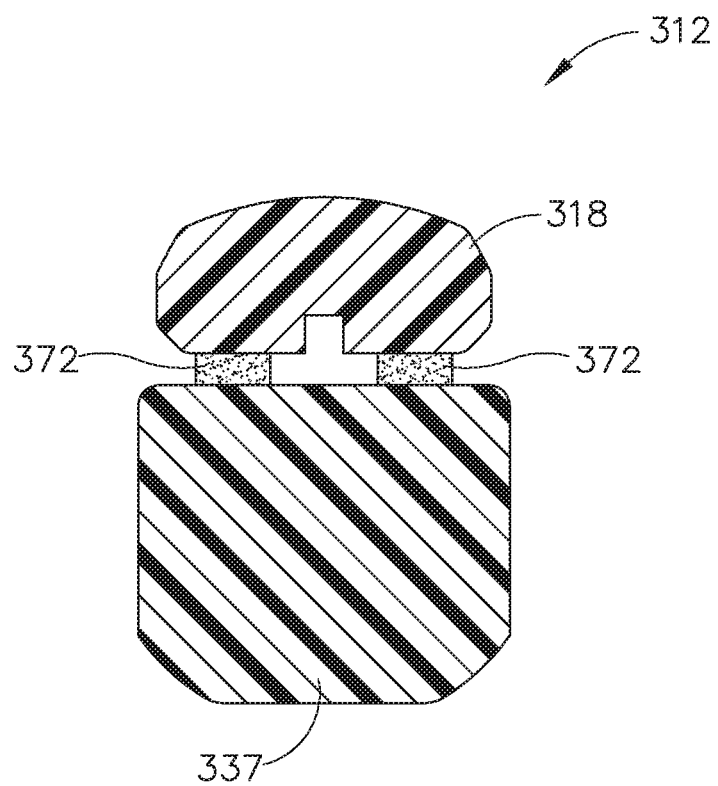
FIG. 20 depicts a cross-sectional view taken along the line 20-20 of FIG. 19 showing the lateral stabilization members.

Lateral stabilization members (372) may also be seen in FIG. 19, and furthermore a front, cross sectional view of lateral stabilization members (372) may be seen in FIG. 20. Lateral stabilization members (372) comprise pieces of material operable to provide lateral contact between anvil (318) and cartridge (337). As can be seen in FIG. 20, lateral stabilization members (372) include two contact members with a space provided therebetween. It will be appreciated that by placing lateral stabilization members (372) at opposite lateral sides of anvil (318) and cartridge (337), when anvil (318) closes on cartridge (337) during use, anvil (318) comes into contact with lateral stabilization members (372). When in contact with lateral stabilization members (372), anvil (318) becomes laterally stabilized such that anvil (318) does not rock left or right relative to cartridge (337). In particular, lateral stabilization member (372) provides a surface of contact along lateral stabilization member (372) for anvil (318) to engage. As a result, it will be understood that as anvil (318) closes on cartridge (337), even though anvil (318) may roll laterally due to pressing against tissue of various thicknesses or densities, anvil (318) laterally straightens once anvil (318) closes against lateral stabilization members (372). Lateral stabilization members (372) thus function similar to protrusions (250) of FIG. 13. In some exemplary versions, lateral stabilization members (372) may be positioned on anvil (318) rather than cartridge (337). In yet other exemplary versions, lateral stabilization members (372) may be placed on both anvil (318) and cartridge (337). Other suitable versions of lateral stabilization members (372) will be apparent to one of ordinary skill in the art in view of the teachings herein. It will be appreciated that in some versions, lateral stabilization members (372) and/or alignment member (370) may be used in conjunction with end effector (212) shown in FIG. 13, thereby providing further added stabilization.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI® system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, now U.S. Pat. No. 8,844,789, issued Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, now U.S. Pat. No. 8,820,605, issued Sep. 2, 2014, the disclosure of which is incorporated by reference herein; U.S. Pub. No. 2012/0132450, entitled "Shiftable Drive Interface for Robotically-Controlled Surgical Tool," published May 31, 2012, now U.S. Pat. No. 8,616,431, issued Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, now U.S. Pat. No. 8,573,461, issued Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, now U.S. Pat. No. 8,602,288, issued Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No. 9,301,759, issued Apr. 5, 2016, the disclosure of which is incorporated by reference herein; U.S. Pub. No. 2012/0203247, entitled "Robotically-Controlled Surgical End Effector System," published Aug. 9, 2012, now U.S. Pat. No. 8,783,541, issued Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012 now U.S. Pat. No. 8,479,969, issued Jul. 9, 2013; U.S. Pub. No. 2012/0138660, entitled "Robotically-Controlled Cable-Based Surgical End Effectors," published Jun. 7, 2012, now U.S. Pat. No. 8,800,838, issued Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, now U.S. Pat. No. 8,573,465, issued Nov. 5, 2013 the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
(a) a body; and
(b) an end effector in communication with the body, wherein the end effector comprises:

(i) a stapling jaw defining a longitudinal axis, the stapling jaw comprising a first distal end and a deck, (ii) an anvil comprising a second distal, wherein the anvil is configured to pivot relative to the stapling jaw from an open configuration to a closed configuration, wherein the anvil and the deck are configured to capture tissue when the anvil is in the closed configuration, and (iii) a stabilization assembly associated with the first distal end of the stapling jaw and the second distal end of the anvil, wherein the stabilization assembly is configured to laterally align the anvil relative to the stapling jaw, in the closed configuration, by inhibiting lateral pivotal deflection of the anvil relative to the longitudinal axis, the stabilization assembly comprising:

(A) an elongated semi-spherical groove comprising a first length and a first width, and (B) a protrusion comprising a second length and a second width, wherein the second length is smaller than the first length, wherein the second width complements the first width such that the second width is smaller than or equal to the first width of the elongated semi-spherical groove, wherein the protrusion is configured to slide into the elongated semi-spherical groove as the anvil pivots into the closed configuration.

2. The apparatus of claim 1, wherein the deck defines a plurality of apertures of wherein each aperture of the plurality of apertures houses a respective staple.

3. The apparatus of claim 2, wherein the anvil defines a plurality of staple forming pockets, wherein the stabilization assembly is configured to laterally align the plurality of staple forming pockets with a respective aperture of the plurality of apertures when the anvil is in the closed configuration.

4. The apparatus of claim 3, further comprising a firing assembly configured to drive the staples housed within the plurality of apertures toward the plurality of staple forming pockets.

5. The apparatus of claim 4, wherein the firing assembly is further configured to sever tissue captured between the anvil and the deck.

6. The apparatus of claim 3, further comprising an articulation control configured to drive deflection of the articulation joint.

7. The apparatus of claim 1, wherein the elongated semi-spherical groove comprises a straight curved portion, a first spherical curved portion, and a second spherical curved portion, wherein the straight curved portion is interposed between the first spherical curved portion and the second spherical curved portion.

8. The apparatus of claim 7, wherein the protrusion is configured to engage either the first spherical curved portion of the second spherical curved position and then slide toward into the straight curved portion as the anvil pivots toward the closed configuration.

9. The apparatus of claim 1, wherein the elongated semi-spherical groove is associated with the anvil.

10. The apparatus of claim 9, wherein the elongated semi-spherical groove is laterally centered along the anvil.

11. The apparatus of claim 10, wherein the protrusion is associated with the stapling jaw.

12. The apparatus of claim 11, wherein the anvil is shaped to laterally taper toward engagement groove.

13. The apparatus of claim 1, wherein the protrusion comprises a semi-spherical shape.

14. The apparatus of claim 1, further comprising a shaft assembly extending from the body toward the end effector.

15. The apparatus of claim 14, wherein the shaft assembly comprise an articulation joint configured to deflect the end effector relative to the body.

16. The apparatus of claim 1, wherein the first length and the second length extend along the longitudinal axis while the anvil is in the closed configuration.

17. An apparatus comprising:

(a) a shaft assembly; and (b) an end effector extending distally from the shaft assembly, wherein the end effector comprises:

(i) a cartridge defining a longitudinal axis, the cartridge comprising a first distal end and a deck, (ii) an anvil comprising a second distal, wherein the anvil is configured to pivot relative to the cartridge from an open configuration to a closed configuration, wherein the anvil and the deck are configured to capture tissue when the anvil is in the closed configuration, and (iii) a stabilization assembly associated with the first distal end of the cartridge and the second distal end of the anvil, wherein the stabilization assembly comprises:

(A) an elongated semi-spherical groove comprising a first length extending in a longitudinal direction while the anvil is in the closed configuration, and (B) a protrusion comprising a second length extending in the longitudinal direction while the anvil is in the closed configuration, wherein the second length is smaller than the first length, wherein the protrusion is configured to engage the elongated semi-spherical groove to laterally align the anvil relative to the cartridge, in the closed configuration, by inhibiting lateral pivotal deflection of the anvil relative to the longitudinal axis.

18. The apparatus of claim 17, wherein the protrusion is configured to slide along the elongated semi-spherical groove while engaging the elongated semi-spherical groove.

19. The apparatus of claim 18, wherein the protrusion comprises a diameter that complements a width of the elongated semispherical groove.

20. An apparatus comprising:

(a) a shaft assembly; and (b) an end effector extending distally from the shaft assembly, wherein the end effector comprises:

(i) a cartridge defining a longitudinal axis, the cartridge comprising a first distal end and a deck, (ii) an anvil comprising a second distal, wherein the anvil is configured to pivot relative to the cartridge from an open configuration to a closed configuration, wherein the anvil and the deck are configured to capture tissue when the anvil is in the closed configuration, and (iii) a stabilization assembly associated with the first distal end of the cartridge and the second distal end of the anvil, wherein the stabilization assembly comprises:

(A) an elongated groove comprising a first length extending in a longitudinal direction and terminating into a spherical curved portion, and (B) a protrusion comprising a second length extending in the longitudinal direction, wherein the second length is smaller than the first length, wherein the protrusion is configured to engage the spherical curved portion and slide away from the spherical curved portion into an adjacent portion into the straight curved portion of the elongated groove, as the anvil pivots toward the closed configuration, to laterally align the anvil relative to the cartridge, thereby inhibiting lateral pivotal deflection of the anvil relative to the longitudinal axis.

\* \* \* \* \*